(12) United States Patent
Parrott

(10) Patent No.: US 9,187,385 B1
(45) Date of Patent: Nov. 17, 2015

(54) CHARCOAL IGNITION FLUID

(71) Applicant: BioPolymer Industries, Inc., Tulsa, OK (US)

(72) Inventor: Paul Ray Parrott, Catoosa, OK (US)

(73) Assignee: InnoVerdant, LLC, Tulsa, OK (US)

( * ) Notice: Subject to any disclaimer, the term of this patent is extended or adjusted under 35 U.S.C. 154(b) by 89 days.

(21) Appl. No.: 13/648,103

(22) Filed: Oct. 9, 2012

Related U.S. Application Data

(60) Provisional application No. 61/544,794, filed on Oct. 7, 2011.

(51) Int. Cl.
*C07C 9/00* (2006.01)
*C07C 9/14* (2006.01)

(52) U.S. Cl.
CPC .................................. *C07C 9/00* (2013.01)

(58) Field of Classification Search
CPC .............................................. C07C 9/00–9/22
See application file for complete search history.

(56) References Cited

U.S. PATENT DOCUMENTS

| | | | |
|---|---|---|---|
| 4,778,826 A | 10/1988 | Jezl et al. | |
| 5,276,231 A * | 1/1994 | Kocal et al. | 585/323 |
| 6,056,793 A | 5/2000 | Suppes | |
| 6,787,577 B2 | 9/2004 | Davis et al. | |
| 6,843,812 B2 * | 1/2005 | Stephanos | 44/266 |
| 7,294,253 B2 | 11/2007 | DeHaan et al. | |
| RE40,419 E | 7/2008 | Norbek et al. | |
| 7,632,318 B2 | 12/2009 | Stephanos | |
| 7,846,323 B2 | 12/2010 | Abhari et al. | |
| 7,972,392 B2 | 7/2011 | Eichhorn et al. | |
| 2004/0231237 A1 | 11/2004 | Boer et al. | |
| 2009/0293345 A1 | 12/2009 | Esen et al. | |
| 2011/0008507 A1 | 1/2011 | Moe et al. | |
| 2011/0107947 A1 | 5/2011 | Vernon | |
| 2011/0269654 A1 | 11/2011 | Marlin | |
| 2012/0157725 A1 * | 6/2012 | McAuliffe | 585/16 |

OTHER PUBLICATIONS

Gautam, M. et al. (1999). "Combustion Characteristics of Higher Alcohol/Gasoline Blends," in The Economical Production of Alcohol Fuels from Coal-Derived Synthesis Gas, U.S. Department of Energy, TR-25 & TR-26, pp. 377-409.*

* cited by examiner

*Primary Examiner* — Brian McCaig
(74) *Attorney, Agent, or Firm* — Head, Johnson & Kachigan, P.C.

(57) ABSTRACT

A charcoal ignition fluid that is composed of a blend of bio-based hydrocarbons for the ignition of charcoal in both briquette and lump forms. The charcoal ignition fluid utilizes linear and branched alkanes produced by means of variations of the Fischer-Tropsch process that incorporates raw materials that are generally recognized as more sustainable than petroleum oil. The process for producing the charcoal ignition fluid deoxygenates fatty acids, esters, etc. by removing and fully saturating all double bonds in the bioactive raw materials.

6 Claims, No Drawings

CHARCOAL IGNITION FLUID

CROSS REFERENCE TO RELATED APPLICATIONS

This application claims priority to and the benefit of U.S. Provisional Patent Application Ser. No. 61/544,794, filed Oct. 7, 2011, which is incorporated herein by reference in its entirety.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

REFERENCE TO A SEQUENCE LISTING, A TABLE, OR A COMPUTER PROGRAM LISTING APPENDIX

Not Applicable.

BACKGROUND OF THE INVENTION

1. Field of the Invention

This invention relates generally to a charcoal ignition fluid that is composed of a blend of bio-based hydrocarbons for the ignition of charcoal in both briquette and lump forms, and more particularly, a charcoal ignition fluid that utilizes linear and branched alkanes produced by means of variations of the Fischer-Tropsch process that incorporates raw materials that are generally recognized as more sustainable than petroleum oil.

2. Description of the Related Art

The petroleum-based charcoal starter fluid that is most widely in use is a petroleum distillate that contains significant levels of aromatic and sulfur-containing compounds, which may affect the quality and safety of food cooked over charcoal ignited with this fluid. Additionally, the petroleum distillate charcoal starter fluids consume a significant quantity of petroleum, a non-renewable fossil fuel.

Charcoal starter fluids incorporating petroleum distillates currently in use have a number of drawbacks relative to consumer and environmental issues. For example, they contain a significant and potentially toxic amount of aromatic compounds. Consumers who do not wait until these toxic compounds burn off adequately before placing food over charcoal ignited with petroleum distillates may unknowingly contaminate the food with residues from the incomplete combustion of the fluid still contained in the charcoal. The sulfur-containing compounds in petroleum distillate can also form noxious odors and flavors that are absorbed by food placed in a charcoal cooker.

In order to be easily ignited, the charcoal starter fluid composed of petroleum distillates must have a flashpoint that is low enough, typically 103° F. to 107° F. (Tag Closed Cup). Charcoal starter fluids with flashpoints below 100° F. are more regulated based on being more hazardous to use. Charcoal starter fluids with flashpoints higher than 110° F. are typically too difficult to be ignited, and are therefore, not accepted by consumers.

The presence of certain hydrocarbon species in petroleum-based, charcoal starter fluid causes it to emit significant levels of volatile organic compounds ("VOC") into the atmosphere. The presence of aromatic and cyclic hydrocarbons produce evaporative emissions prior to ignition, as well as those caused by incomplete combustion after ignition. A charcoal starter fluid that does not contain a significant amount of these compounds and that contains higher levels of hydrocarbons that undergo more complete combustion when ignited produce much lower emissions of VOCs.

It is therefore desirable to provide a charcoal ignition fluid that is composed of a blend of renewable bio-based hydrocarbons for the ignition of charcoal in both briquette and lump forms.

It is further desirable to provide a charcoal ignition fluid that utilizes linear and branched alkanes produced by means of variations of the Fischer-Tropsch process that incorporates raw materials that are generally recognized as more sustainable than petroleum oil.

It is further desirable to provide a charcoal ignition fluid that replaces the petroleum distillate currently in wide use as a means of igniting charcoal in both briquettes and lump forms.

It is yet further desirable to provide a charcoal ignition fluid that replaces the hydrocarbon made from petroleum, a non-renewable resource, by mimicking the physical characteristics of the distillate so closely that the typical consumer can use it in the same manner to which they are accustomed when using petroleum distillate.

It is still further desirable to provide a charcoal ignition fluid that is lower in noxious odors and the tendency to product off-flavors compared to petroleum distillate-based charcoal starter fluids.

It is yet further desirable to provide a charcoal ignition fluid having a renewable status that makes it more sustainable on a raw material basis.

It is still yet further desirable to provide a charcoal ignition fluid having a decreased toxicity concern due to the absence of aromatic compounds, such as toluene, xylene, and benzene.

It is still yet further desirable to provide a charcoal ignition fluid composed without aromatic and sulfur compounds, which can affect the flavor and odor of foods cooked over charcoal.

It is still yet further desirable to provide a charcoal ignition fluid that meets VOC emission levels that are permissible according to the South Coast Air Quality Management District Rule 1174 (1991).

Other advantages and features will be apparent from the following description, and from the claims.

SUMMARY OF THE INVENTION

In general, in a first aspect, the invention relates to a process of producing a charcoal ignition fluid. The process includes the steps of first hydrotreating a renewable feedstock with a $C_{4-24}$ isoparaffinic diluent to produce an n-paraffinic fraction. The renewable feedstock includes triglycerides, free fatty acids or combinations thereof, and may be selected from the group consisting of animal fats, animal oils, vegetable fats, vegetable oils, rendered fats, restaurant grease, waste industrial frying oils, fish oils or combinations thereof. The n-paraffinic fraction is then hydroisomerized to produce an isoparaffinic fraction and a heavy fraction. The isoparaffinic fraction is blended with paraffin at a predetermined ratio to form an isoparaffinic blend. Lastly, the isoparaffinic blend is fractionated by boiling point to produce the charcoal ignition fluid having predetermined cloud point and pour point characteristics, such the charcoal ignition fluid having approximately 70% by weight linear and branched $C_{7-18}$-alkanes.

The hydrotreating step can also include hydrotreating the feedstock with the diluent at a reaction temperature of from about 300° F. to about 850° F. and a reaction pressure of from about 250 psig to about 3000 psig. The hydrotreating step may also be carried out in the presence of a sulfide bimetallic catalyst, namely nickel-molybdenum. The hydroisomerizing step can include hydroisomerizing the fraction at a reaction temperature of from about 300° F. to about 850° F. and a reaction pressure of from about 250 psig to about 3000 psig. In addition, the isoparaffinic fraction can have a boiling point range of from about 144° C. to about 277° C., and more particularly between 177° C. and about 260° C. In addition, the process the fractionating step can include the isoparaffinic blend is being carried out in the presence of an oxygenated bio-based hydrocarbon, such as bio-butanol or bio-pentanol, for lowering the cloud point and pour point characteristics.

In general, in a second aspect, the invention relates to a charcoal ignition fluid produced by the modified Fischer-Tropsch process described above.

In general, in a third aspect, the invention relates to a charcoal ignition fluid having approximately 70% by weight linear and branched $C_{5-24}$ alkanes. The charcoal ignition fluid can further include approximately 10% by weight linear and branched $C_{5-8}$ alkanes, approximately 10% by weight linear and branched $C_{9-11}$ alkanes, approximately 20% by weight linear and branched $C_{12-14}$ alkanes and approximately 20% by weight linear and branched $C_{15-24}$ alkanes.

In addition, the charcoal ignition fluid can be approximately 95% to approximately 97% by weight linear and branched $C_{5-20}$ alkanes and approximately 3% to approximately 5% by weight bio-butanol. Alternatively, the charcoal ignition fluid can include approximately 94% to approximately 97% by weight linear and branched $C_{5-20}$ alkanes and approximately 3% to approximately 6% by weight bio-pentanol.

Moreover, the charcoal ignition fluid may have the following physical properties: a viscosity at 40° C. of approximately 1.4 to approximately 4.1 cp; a flash point of approximately 39° C. to approximately 43° C.; a density at 15° C. of approximately 0.75 to approximately 0.78 g/ml; an auto-ignition temperature of approximately 257° C.; a vapor pressure at 20° C. of approximately <0.3 kPa; a boiling point of approximately 127° C. to approximately 288° C.; and a freezing point of approximately −40° C. The charcoal ignition fluid contains no toxic aromatic compounds, such as xylene, toluene or benzene, or sulfur compounds.

DETAILED DESCRIPTION OF THE INVENTION

The compounds and methods discussed herein are merely illustrative of specific manners in which to make and use this invention and are not to be interpreted as limiting in scope.

While the compounds and methods have been described with a certain degree of particularity, it is to be noted that many modifications may be made in the selection and the arrangement of the chemical and function details disclosed herein without departing from the spirit and scope of this disclosure. It is understood that the compounds and methods are not limited to the embodiments set forth herein for purposes of exemplification.

A charcoal ignition fluid is provided that is composed of a blend of bio-based hydrocarbons for the ignition of charcoal in both briquette and lump forms. The charcoal ignition fluid utilizes linear and branched alkanes produced by means of variations of the Fischer-Tropsch process that incorporates raw materials that are generally recognized as more sustainable than petroleum oil. The charcoal ignition fluid mimics the physical properties of petroleum distillate and matches or surpasses the consumer appeal of petroleum distillate based on the absence of noxious odors.

A process of producing the charcoal ignition fluid is also provided. The process uses a modified Fischer-Tropsch process to produce a mixture of alkanes. The raw materials for the process include sustainable sources, such as renewable feedstocks of animal fats, animal oils, vegetable fats, vegetable oils, rendered fats, restaurant grease, waste industrial frying oils, fish oils, and combinations thereof, along with other biomass from agricultural and non-agricultural sources. The selected feedstock is hydrotreated to produce normal paraffins that are separated into a distinct boiling range and cloud point. In particular, the Fischer-Tropsch process provided herein involves a deoxygenation/hydrotreating step that results in fractions containing normal paraffins. A portion of the normal paraffins, especially the heavier fraction, are then hydroisomerized to produce isoparaffins. The resulting isoparaffins can subsequently be fractionated into a predetermined boiling range. In order to achieve predetermined cloud point and pour point characteristics, the resulting mixed normal and isoparaffins are fractionated using a proper ratio in a distillation column to produce the charcoal ignition fluid having suitable properties to replace petroleum-based odorless kerosene when used in the same manner to ignite charcoal.

The charcoal ignition fluid and related process provide a number of benefits relative to petroleum-based ignition fluids due to the absence of toxic aromatic compounds and sulfur. The charcoal ignition fluid contains no toxic aromatic compounds, such as xylene, toluene and benzene, which may be present in petroleum-based ignition fluids. In addition, other compounds found in petroleum kerosene, such as organic sulfur compounds, are also absent from the charcoal ignition fluid provided herein.

The charcoal ignition fluid may have the composition as outlined below in Table 1 or Table 2.

TABLE 1

Composition Specification

| Blend Composition | Vol. % | Distillation Range |
| --- | --- | --- |
| ALKANE $C_{5-8}$ | 10% | 144-177° C. |
| ALKANE $C_{9-11}$ | 10% | 177-191° C. |
| ALKANE $C_{12-14}$ | 20% | 191-220° C. |
| ALKANE $C_{15-24}$ | 50% | 220-270° C. |

TABLE 2

Composition Specification

| Component | Weight % |
| --- | --- |
| $C_{7-18}$-alkane branched | approximately > 70 |
| Proprietary Compounds | approximately > 20 |
| May contain up to 30 wt % performance additive(s). | |

The charcoal ignition fluid may include the physical properties as outlined below in Table 3.

TABLE 3

Physical Properties

| | |
|---|---|
| Viscosity at 40° C. | approximately 1.4 to approximately 4.1 cp |
| Flash Point | approximately 39° C. to approximately 43° C. |
| Density at 15° C. | approximately 0.75 to approximately 0.78 g/ml |
| Color of composition | colorless |
| Auto-ignition Temperature | approximately 257° C. |
| Vapor Pressure at 20° C. | approximately <0.3 kPa |
| Approximate Boiling Range | approximately 127° C. to approximately 288° C. |
| Freezing Point | approximately −40° C. |
| Solubility in water | Insoluble |

The process for blending the charcoal ignition fluid may be determined by each bio-refining facility. While nomenclature may vary by manufacturer, the nomenclature refers to the primarily isoparaffinic alkanes, such as those produced by Dynamic Fuels, LLC (Geismar, La.) from animal and vegetable fats, oils and greases. By way of example, the methods and material utilized for this study of the distillates were produced within the boiling ranges indicated below in Table 4, and relate to the recovery rate from the fractional distillation process.

TABLE 4

Boiling Ranges

| | |
|---|---|
| Initial boiling point | 144° C. |
| 10% recovered | 177° C. |
| 20% recovered | 191° C. |
| 50% recovered | 220° C. |
| 90% recovered | 260° C. |
| Final boiling point | 270-300° C. |

The charcoal ignition fluid disclosed herein utilizes new and emerging hydrocarbon production in the United States and abroad, which results from the demand for more sustainable sources for primarily transportation fuels in order to reduce U.S. dependence on foreign oil. Because the charcoal ignition fluid can be produced from highly sustainable and even renewable sources, it does not diminish the highly sustainable nature of the charcoal ignition fluid. While only a small number of plants exist that are currently able to produce commercial quantities of the specific hydrocarbons from biological and non-petroleum sources, there are more plants being planned and built every year. The rate at which this infrastructure is developing is based on the ability of each variation of Fischer-Tropsch and other emerging processes to produce hydrocarbons that are economically competitive with those produced from petroleum.

Other bio-based hydrocarbons not currently available in commercial quantities may be added to the charcoal ignition fluid disclosed herein in the future as they become more available, as exemplified in the following examples of Tables 5 and 6.

TABLE 5

| | |
|---|---|
| Bio-butanol (Gevo Corp., Englewood, CO) | 3-5% by weight |
| Bio-derived, C5-20 alkane branched and linear | 95-97% by weight |
| Mixture flashpoint | >103° F. |

TABLE 6

| | |
|---|---|
| Bio-pentanol, mixed isomers branched and linear | 3-6% by weight |
| Bio-derived blend of C5-20 alkane | 94-97% by weight |

The charcoal ignition fluid produces a flash point, evaporation rate, low viscosity, and surface tension adequate to effectively mimic the properties of petroleum distillate of the type commonly used as charcoal starter fluid. The yellow flame typically found in petroleum distillate-based charcoal starter fluids is the result of incomplete combustion of the hydrocarbons that comprise petroleum distillate, a cause for concern relative to the emission of toxic compounds and VOC's that can contaminate surfaces contacted by food or the food itself during cooking Some compounds emitted by the burning of petroleum distillate-based charcoal starter fluids have been shown to cause cancer in laboratory animals.

In addition to squirting the ignition fluid onto charcoal or other carbonaceous solid fuel, the method of pre-soaking these materials may be used. In this method, the solid fuel is soaked and drained of excess ignition fluid prior to packaging. The packaging shall be of a type that prevents emission of the volatile portion of the fluid.

The charcoal ignition fluid pours, squirts and absorbs into charcoal briquettes and lump forms in a manner very similar to petroleum distillate-based starter fluids so that the consumer is not required to change any of the habits of handling practices developed as a result of years of using petroleum distillate-based starter fluid. The volatile properties of the charcoal ignition fluid match or diminish the "flash back" characteristic of petroleum distillate-based such that no perceptible change in safety procedures is required. Further, the charcoal ignition fluid can easily be ignited in the same manner as standard charcoal starter fluid (petroleum distillate or kerosene), with a match or butane lighter. In addition, toxicity is greatly reduced as it relates to food contamination and potential poisoning by direct contact with the charcoal ignition fluid, and the charcoal ignition fluid contains hydrocarbons that are more completely oxidized and therefore contributes lower levels of VOCs to the atmosphere, in the case of formulations that include bio-butanol or bio-pentanol. Because oxygen is contained in the molecular structure of the charcoal ignition fluid, its combustion is more efficient than un-oxygenated hydrocarbons, such as those contained in petroleum distillate-based starter fluids.

Moreover, the charcoal ignition fluid does not contain cyclic hydrocarbons, such as toluene, xylene, and benzene, which are more toxic to humans. The animal and vegetable fats, oils and greases from which the charcoal ignition fluid is produced reduce the United States dependence on foreign oil. In fact, the current production of bio-based hydrocarbons of the type used in the charcoal ignition fluid disclosed herein are adequate to satisfy the entire projected requirement in the United States, whereas this same production will satisfy only a small fraction of the demand for transportation fuel.

Furthermore, the somewhat noxious odor of petroleum distillate-based starter fluids is replaced by a lower, less offensive odor with a slightly "sweet" odor. Also, unlike petroleum distillate-based starter fluids, which produce relatively high levels of black smoke when ignited, the charcoal ignition fluid produces much less smoke and may find additional use as a means of starting wood in indoor fireplaces and in wood pellet heaters. Additionally unlike petroleum distillate-based starter fluids, the charcoal ignition fluid can be recycled and stored in a polyethylene terephthalate (PET) container, which is easily recycled when empty. Petroleum distillate-based starter fluids must be packaged in either a metal can (hard to squeeze) or polyvinyl chloride plastic bottles. The bio-alcohols that may be used in the charcoal ignition fluid are readily biodegraded to prevent any residual contamination of the environment in the event of a spill or accidental release. In addition, because of the charcoal ignition fluid is made using a modification of a process for making fuel grade isoparaffinic alkanes, the charcoal ignition fluid is capable of being priced competitively with petroleum distillate-based starter fluids, a first for an environmentally friendly product of this type.

EXAMPLES

The following examples illustrate the invention.

Example 1

The process by which animal fats are converted to normal paraffins is described in U.S. Pat. No. 7,846,323 entitled "Process for Co-Producing Jet Fuel and LPG from Renewable Resources," issued to Syntroleum Corporation (Tulsa, Okla.), which is expressly incorporated herein in its entirety. The renewable feedstock is placed in a reactor and converted to n-paraffins using a hydrotreating process with a nickel-molybdenum as a catalyst. Based on the cloud point of the resulting hydrocarbon liquid, a portion is then hydroisomerized to produce an isoparaffinic product that, when blended properly with the normal paraffin, can be fractionated to the proper boiling range for the charcoal ignition fluid detailed in Table 1 above. The carbon number distribution would be C6-C18 for paraffinic alkanes derived from this raw material using this particular Fisher-Tropsch process.

Example 2

The same process described in Example 1 is modified such that the normal paraffin resulting from the initial hydrotreating stage is fractionated before being blended with the isoparaffin resulting from the hydroisomerization step, which can be fractionated separately. In this example, the cloud point of the final product can be determined without the need to make adjustments after fractionation.

Example 3

A test was conducted with the charcoal ignition fluid and an odorless kerosene ignition fluid used as a control. The test involved decanting 100 ml of ignition fluid onto twenty-four (24) charcoal briquettes stacked in the same manner for both the test of the charcoal ignition fluid and the control. This test was conducted on three (3) separate occasions when the air temperature was 40° F., 74° F. and 107° F. In each test, the time was measured from the point of ignition until the charcoal was considered adequately ignited to begin cooking. In each case, the performance of the charcoal ignition fluid was equal to or better than that of the kerosene ignition fluid.

Whereas, the compounds and methods have been described in relation to the drawings and claims, it should be understood that other and further modifications, apart from those shown or suggested herein, may be made within the spirit and scope of this invention.

What is claimed is:

1. A charcoal ignition fluid, comprising:
    approximately 10% by volume linear and branched $C_{5-8}$ alkanes;
    approximately 10% by volume linear and branched $C_{9-11}$ alkanes;
    approximately 20% by volume linear and branched $C_{12-14}$ alkanes; and
    approximately 50% by volume linear and branched $C_{15-24}$ alkanes.

2. The charcoal ignition fluid of claim 1 wherein said charcoal ignition fluid further comprises approximately 3% to approximately 5% by weight bio-butanol.

3. The charcoal ignition fluid of claim 1 wherein said charcoal ignition fluid further comprises approximately 3% to approximately 6% by weight bio-pentanol.

4. The charcoal ignition fluid of claim 1 wherein physical properties of said fluid comprise:
    a viscosity at 40° C. of approximately 1.4 to approximately 4.1 cp;
    a flash point of approximately 39° C. to approximately 43° C.;
    a density at 15° C. of approximately 0.75 to approximately 0.78 g/ml;
    an auto-ignition temperature of approximately 257° C.;
    a vapor pressure at 20° C. of approximately <0.3 kPa;
    a boiling point of approximately 127° C. to approximately 288° C.; and
    a freezing point of approximately −40° C.

5. The charcoal ignition fluid of claim 1 wherein said charcoal ignition fluid contains no toxic aromatic compounds or sulfur compounds.

6. The charcoal ignition fluid of claim 5 wherein said charcoal ignition fluid contains no xylene, toluene or benzene.

* * * * *